United States Patent
Konecke

(10) Patent No.: US 6,663,831 B2
(45) Date of Patent: Dec. 16, 2003

(54) "ONE-DEVICE" SYSTEM FOR TESTING CONSTITUENTS IN FLUIDS

(75) Inventor: Jeffery A. Konecke, Mebane, NC (US)

(73) Assignee: Forefront Diagnostics, Inc., Laguna Hills, CA (US)

(*) Notice: Subject to any disclaimer, the term of this patent is extended or adjusted under 35 U.S.C. 154(b) by 258 days.

(21) Appl. No.: 09/825,778

(22) Filed: Apr. 4, 2001

(65) Prior Publication Data

US 2002/0146346 A1 Oct. 10, 2002

(51) Int. Cl.[7] .................................................. G01N 33/48
(52) U.S. Cl. ........................... 422/58; 422/61; 422/102; 436/164; 436/169
(58) Field of Search ............................. 422/56, 58, 61, 422/102; 436/164, 169

(56) References Cited

U.S. PATENT DOCUMENTS

| | | | |
|---|---|---|---|
| 3,915,639 A | 10/1975 | Friedenberg | |
| 4,231,923 A | 11/1980 | Miller et al. | |
| 4,431,742 A | 2/1984 | Rosenblatt | |
| 4,774,192 A | 9/1988 | Terminiello et al. | |
| 4,843,377 A | 6/1989 | Fuller et al. | |
| 4,844,866 A | 7/1989 | Wallace et al. | |
| 4,963,325 A | * 10/1990 | Lennon et al. ................. | 422/61 |
| 4,997,771 A | 3/1991 | Barnett et al. | |
| 5,022,409 A | 6/1991 | Goldstein et al. | |
| 5,073,340 A | 12/1991 | Covington et al. | |
| 5,075,078 A | 12/1991 | Osikowicz et al. | |
| 5,079,141 A | 1/1992 | Niskanen et al. | |
| 5,101,015 A | 3/1992 | Brynes et al. | |
| 5,103,836 A | 4/1992 | Goldstein et al. | |
| 5,140,161 A | 8/1992 | Hillman et al. | |
| 5,234,001 A | 8/1993 | Goldstein et al. | |
| 5,238,652 A | 8/1993 | Sun et al. | |
| 5,244,815 A | 9/1993 | Guirguis | |
| 5,260,031 A | 11/1993 | Seymour | |
| 5,260,194 A | 11/1993 | Olson | |
| 5,304,479 A | 4/1994 | Lin et al. | |
| 5,334,502 A | 8/1994 | Sangha | |
| 5,335,673 A | 8/1994 | Goldstein et al. | |
| 5,339,829 A | 8/1994 | Thieme et al. | |
| 5,479,937 A | 1/1996 | Thieme et al. | |
| 5,573,009 A | 11/1996 | Thieme et al. | |
| 5,583,003 A | 12/1996 | Hillyard et al. | |
| 5,656,448 A | 8/1997 | Kang et al. | |
| 5,705,353 A | 1/1998 | Oh et al. | |
| 5,714,341 A | 2/1998 | Thieme et al. | |
| 5,736,322 A | 4/1998 | Goldstein | |
| 5,817,011 A | 10/1998 | Schoendorfer | |
| 5,830,410 A | 11/1998 | Thieme et al. | |
| 5,871,905 A | 2/1999 | Thieme et al. | |
| 5,955,377 A | 9/1999 | Maul et al. | |
| 5,968,746 A | 10/1999 | Schneider | |
| 6,022,326 A | 2/2000 | Tatum | |
| 6,372,516 B1 | 4/2002 | Sun | |

* cited by examiner

Primary Examiner—Lyle A. Alexander
(74) Attorney, Agent, or Firm—Knobbe, Martens, Olson & Bear, LLP

(57) ABSTRACT

A "one-device" system and method for collecting, extracting testing, and confirming various constituents in fluids is described. Particularly, it relates to the detection of various drugs of abuse in bodily fluids. More particularly, it collects and performs assay of a human's saliva, sweat, urine or other bodily fluid sample to test and/or confirm for drugs of abuse. In a preferred embodiment, the bodily fluid is collected via a collection end of the device, a series of pressure heads inside the cap of the collection device forces the sample, as the collection end of the device passes through the pressure heads, into the core of an immunoassay system containing diagnostic strips for illegal drug detection. Furthermore, a portion of the sample is retained in a confirmation sample retention well, which is seal from the outside, allowing some samples to be sent, such as to a laboratory, for testing later.

14 Claims, 8 Drawing Sheets

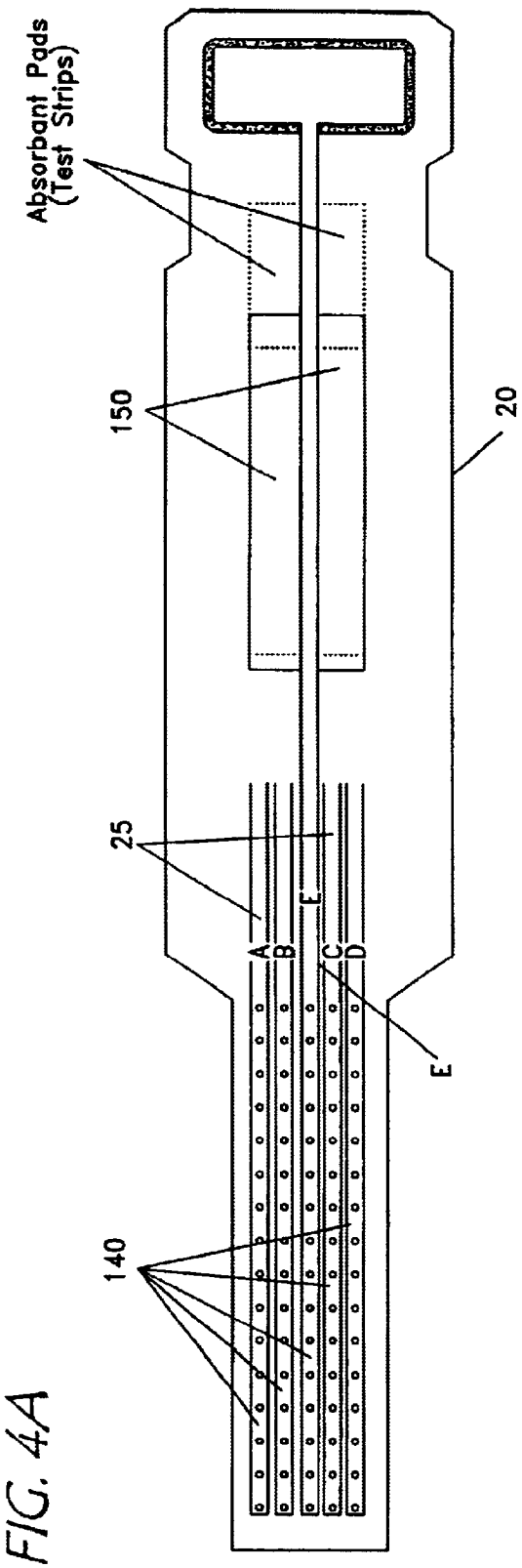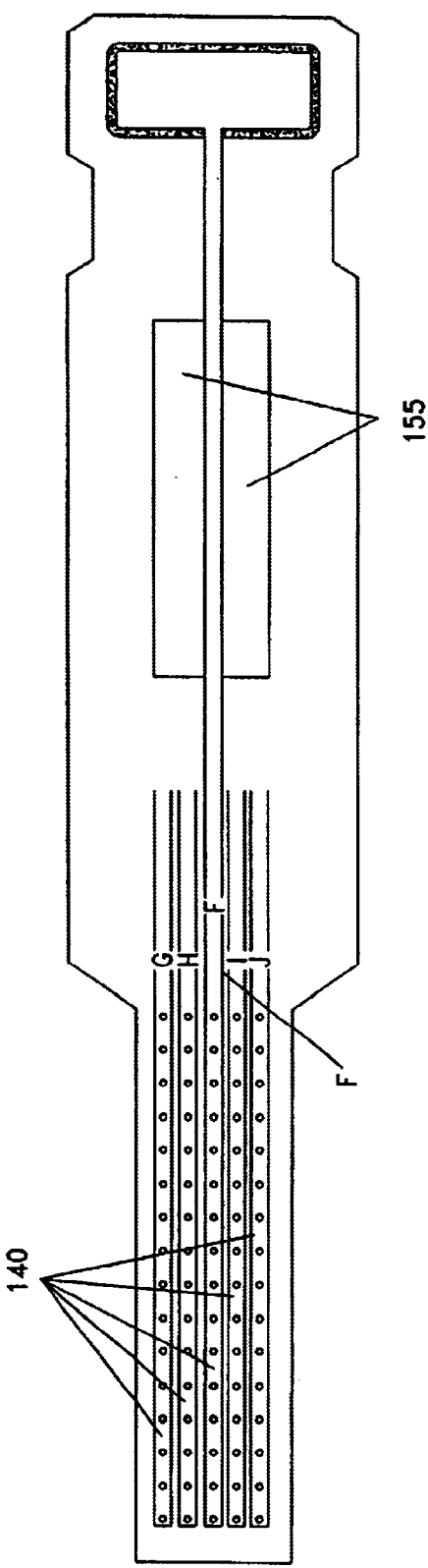
FIG. 4A
FIG. 4B

"ONE-DEVICE" SYSTEM FOR TESTING CONSTITUENTS IN FLUIDS

FIELD OF THE INVENTION

This invention relates to a "one device" system and method for collecting, extracting, testing, and confirming various constituents in fluids. In particular, this system is suitable for detecting drugs of abuse in bodily fluids. In one embodiment, the system is used to collect a human's saliva, sweat, urine, blood or other bodily fluid sample to test and/or confirm for drugs of abuse. In a preferred embodiment, the bodily fluid is collected via a collection end of the device with an absorbent pad, a series of pressure heads inside the cap of the collection device forces the sample (as the collection end of the device passes through the pressure heads) into the core of an immunoassay system containing diagnostic strips for drug of abuse detection. The drug in the sample competes with a drug conjugate immobilized on a membrane support for limited antibody sites on colored micro-spheres. A colored line indicates the presence or absence of illegal drugs in the sample. Furthermore, a portion of the sample is retained in a confirmation sample retention well, which is seal from the outside allowing samples stored for further testing.

BACKGROUND OF THE INVENTION

A number of devices and methods are commonly available to collect, extract, or test for various constituents in fluids. However, these devices require separate collection, extraction and testing of the sample. This device is designed to combine these three key functions into one device. Generally, fluids include saliva, urine, blood, sweat or other bodily fluids. The constituents include the detection for the presence of drugs of abuse, toxins, alcohols, glucose, cholesterol, urea, antigen or antibody, etc.

DESCRIPTION OF THE PRIOR ART

U.S. Pat. No. 4,431,742 to Rosenblatt describes a radio-receptor assay for benzodiazpines in saliva which comprises measuring the diminution of attachment of a know quantity of radio labeled benzodiazepine to a receptor carrier in the presence of an unknown quantity of unlabeled benzodiazepine in a known amount of human saliva.

U.S. Pat. Nos. 5,339,829, 5,479,937, 5,573,009, and 5,830,410 to Thieme et al describe a device for obtaining oral fluid containing substances for testing that includes a syringe having a plunger at the end of which an absorbent pad is attached.

U. S. Pat. No. 5,714,341 to Thieme et al describes an improved method for determining the presence of an analyte in an oral fluid sample. A portion of the sample is mixed or contacted with a chromogenic substrate effective to produce a colored product upon reaction with α-amylase present in the sample.

U.S. Pat. No. 5,736,322 to Goldstein describes a substitute oral fluid standard for testing, calibration, and standardization of devices and methods for collection, storage, and analysis or oral fluids. The oral fluid standard comprises a mucin and protease inhibitor.

U.S. Pat. No. 5,705,353 to Oh et al describes an assay for determining the presence of an analyte of interest in a test sample containing an interfering substance that interferes with the assay is disclosed. The assay comprises the steps of forming a reaction mixture by combining in an assay medium (i) an assay system containing components for detecting the analyte of interest, (ii) a test sample containing the analyte and an interfering substance, and (iii) an additional amount of the interfering substance in a quantity sufficient to substantially mask the effect of the interfering substance in the test sample.

U.S. Pat. No. 5,871,905 to Thieme et al describes the use and composition of materials which, when added to oral fluid samples, make such sample suitable for use with microparticle-based immunoassays. The method involves providing an oral fluid sample combined with a bile acid or salt to reduce the rate of occurrence of false positives in said oral fluid based immunoassays.

U.S. Pat. No. 3,915,639 to Friedenberg describes a drug abuse compounds that are quantitatively and semi-quantitatively detected by the use of an ion exchange dipstick in combination with a stain-producing reagent, and a stain-intensifying reagent which will intensify the coloring effect of the stain-producing reagent.

U.S. Pat. No. 4,231,923 to Miller et al describes an assay method for opioid activity comprising the steps of (a) incubating together an opiate receptor material, a radio-iodinated structural analogue of leucine-enkephalin or methionine-eukephalin, and a liquid sample; (b) measuring the percentage inhibition of the binding of the radio-iodinated compound to the opiate receptor material; and (c) determining the opioid activity of the liquid sample using the percentage inhibition measurement.

U.S. Pat. No. 4,997,771 to Barnett et al describes a method for determining the BZ-1 receptor activity of a test sample or a potential anxiolytic drug.

U.S. Pat. No. 5,073,340 to Covington et al describes a test device for use in determining analyte wherein binder is supported on a solid support in admixture with a marker whereby the presence and location of binder on the support can be determined prior to the assay.

U.S. Pat. No. 5,075,078 to Osikowicz et al describes an improved chromatographic strip binding assay devices provided for determining the presence or amount of an analyte present in a patient sample.

U.S. Pat. No. 5,079,141 to Niskanen et al describes an invention that comprises a pre-filled and pre-sealed apparatus for carrying out chemical, particularly immuno-chemical, analyses in non-laboratory environments.

U.S. Pat. No. 5,101,015 to Brynes et al describes a fluorescence polarization immunoassay (FPIA) for detecting the presence of one or more amphetamine-class analytes in a test sample.

U.S. Pat. No. 5,140,161 to Hillman et al describes methods and devices involving at least one chamber, at least one capillary, and at least one reagent involved in a system providing for a detectable signal.

U.S. Pat. No. 5,238,652 to Sun et al describes an analytical test device for competition assay for particular non-protein antigens, such as antigens representing drugs of abuse.

U.S. Pat. No. 5,244,815 to Guirguis describes a method and device for testing for the presence of substances such as drugs in body fluids while simultaneously positively identifying the test substance.

U.S. Pat. No. 5,304,479 to Lin et al describes a derivatives of phencyclidine provided as precursors for conjugating to antigenic proteins for the preparation of antibodies which bind to phencyclidine or conjugation to enzymes for use as reagents in immunoassays.

U.S. Pat. No. 5,583,003 to Hillyard et al relates to a reagent and a method for detecting an antigen, antibody or other analyte in a sample, such as human or animal blood, by an agglutination assay.

U.S. Pat. No. 5,022,409 to Goldstein et al describes an invention concerning the collection of immunoglobulins from the oral cavity for immunological testing.

U.S. Pat. No. 5,260,031 to Seymour describes a saliva sampling device includes a holder, a saliva collector and an indicator.

U.S. Pat. No. 5,334,502 to Sangha describes a method for rapidly determining during a saliva specimen collection procedure the presence of an amount of saliva, and for verifying that the sample obtained is in fact saliva.

U.S. Pat. No. 5,968,746 to Schneider describes a method and apparatus for the preservation of a saliva sample for use in subsequent quantitative chemical assays.

U.S. Pat. No. 6,022,326 to Tatum et al describes a method and device for automatic or semi-automatic collection of saliva has a mouthpiece on a wand.

U.S. Pat. No. 4,774,192 to Terminiello et al describes a dry chemistry reagent system, kit and method for detection of an analyte such as glucose, cholesterol, urea, antigen or antibody.

U.S. Pat. No. 5,260,194 to Olson describes a method and device for determining the presence of analyte in a sample suspected of containing the analyte.

U.S. Pat. No. 5,656,448 to Kang et al describes an invention pertains to dipstick immunoassay devices.

U.S. Pat. No. 4,843,377 to Fuller et al describes a remote confinement or home arrest system and method which provides for determining from a central office the presence of a prisoner at an assigned remote location such as the prisoner's home and for determining the compliance by the prisoner with behavioral restrictions associated with the confinement such as the abstinence from alcohol or other drugs.

U.S. Pat. No. 4,844,866 to Wallace et al describes a carrier for detecting drug abuse compounds which changes color upon contact with such compounds.

U.S. Pat. No. 5,817,011 to Schoendorfer describes a dermal patch to be worn on the skin for increasing the concentration of an analyte expressed through the skin in perspiration to a conveniently measurable level.

U.S. Pat. No. 5,955,377 to Maul et al describes devices that produce detectable attenuation of the spectral characteristic of light impinging on the device by thin film phenomenon.

U.S. Pat. No. 5,103,836 to Goldstein et al describes a method and device for collecting immunoglobulins and other analytes from the oral cavity for immunological and other testing.

U.S. Pat. No. 5,234,001 to Goldstein et al describes a container for storing collected substances for subsequent testing having an open upper end adapted to be sealed with a removable stopper and a lower end having an opening communicating the interior of the container with the outside.

U.S. Pat. No. 5,335,673 to Goldstein et al describes a method and device for collecting immunoglobulins and other analytes from the oral cavity for immunological and other testing.

In all cases, the normal procedure followed when performing diagnostic test is to collect the sample using either a collection container (for urine or other liquid), a syringe/collection tube (for blood) or some type of collection swab (for saliva, sweat, biological substances or environmental substances). Problems arise when the subject/source can only provide a minimal amount of sample, either because of normal biological restrictions or other reasons. This problem of minimal sample is particularly well documented when the sample to be tested is saliva or sweat. As such, there were generally two possible solutions. One was to collect the sample (i.e. saliva) using an absorbent material and then attempt to "wash" sample off the collection pad in a separate vial containing a buffer/saline solution. The liquid buffer presumably contains the "sample" and is transferred to the test/diagnostic kit either by pouring or pipetting. The second solution would be to collect the sample using an absorbent collection material and then attempt to "squeeze" the sample off the pad and "drop" it directly onto the test device. In all cases, two separate devices and multiple steps are required to perform the test. Additionally, other problems exist, including: sample being contaminated by contact with collector/operator; insufficient "washing" resulting in insufficient sample; exposure to the sample collection material as you try to squeeze if off the pad; and multiple steps leading to operator error in test performance.

SUMMARY OF THE INVENTION

Accordingly, it is an object of the present invention to provide a "one-device" system to collect, transfer, extract, test and retain a portion of the sample to confirm for various constituents in fluids.

It is another object of the present invention to provide a "one-device" system to collect, transfer, extract, test and retain a portion of the sample to confirm for various constituents in fluids with a super absorbent materials for maximum sample collection, wherein the super-absorbent material is selected from a group, comprising gel, foam, fiber glass, cotton, cellulose, rayon and other synthetic materials.

It is another object of the present invention to provide a "one-device" system to collect, transfer, extract, test and retain a portion of the sample to confirm for various constituents in fluids with micro-sample pores for samples to be directly extracted from collection material and transferred to the detection indicator for diagnostic testing.

It is another object of the present invention to provide a "one-device" system to collect, transfer, extract, test and retain a portion of the sample to confirm for various constituents in fluids with a set of pressure heads pressing the sample from the collection end into the micro-pores then onto the detection indicator for testing.

It is another object of the present invention to provide a "one-device" system to collect, transfer, extract, test and retain a portion of the sample to confirm for various constituents in fluids with a series of micro-channels into which the micro-pores are directing the sample to flow through onto the detection indicator for testing.

It is another object of the present invention to provide a "one-device" system to collect, transfer, extract, test and retain a portion of the sample to confirm for various constituents in fluids with sealing fins to which once fluid enters into the fins, the fins will prevent the fluid from leaking out of the system.

It is another object of the present invention to provide a "one-device" system to collect, transfer, extract, test and retain a portion of the sample to confirm for various constituents in fluids with a sample retention well, sealed from the outside allowing samples to be sent later to a laboratory for testing.

It is another object of the present invention to provide a "one-device" system to collect, transfer, extract, test and retain a portion of the sample to confirm for drugs of abuse in bodily fluids wherein the fluid is selected from a group comprising saliva, sweat, urine, blood and other bodily fluids.

It is another object of the present invention to provide a "one-device" system to collect, transfer, extract, test and retain a portion of the sample to confirm for drugs of abuse in bodily fluids with a super absorbent material for maximum sample collection, wherein the super-absorbent material is selected from a group comprising gel, foam, fiber glass, cotton, cellulose, rayon and other synthetic materials.

It is another object of the present invention to provide a "one-device" system to collect, transfer, extract, test and retain a portion of the sample to confirm for drugs of abuse in bodily fluids with micro-sample pores for samples to be directly extracted from collection material and transferred to the strips for diagnostic testing.

It is another object of the present invention to provide a "one-device" system to collect, transfer, extract, test and retain a portion of the sample to confirm for drugs of abuse in bodily fluids with a set of pressure heads pressing the sample from the collection and into the micro pores, then onto immunoassay strips for testing.

It is another object of the present invention to provide a "one-device" system to collect, transfer, extract, test and retain a portion of the sample to confirm for drugs of abuse in bodily fluids with a series of micro-channels into which the micro-pores directing the sample to flow through onto the testing strips.

It is another object of the present invention to provide a "one-device" system to collect, transfer, extract, test and retain a portion of the sample to confirm for various constituents in fluids with a cassette containing chemical strips, to provide an indication of a characteristics of the fluids regarding drugs of abuse, as a detection indicator.

It is another object of the present invention to provide a "one-device" to collect, transfer, extract, test and retain a portion of the sample to confirm for various constituents in fluids with chemical strips used to test for THC, COC, MOR, AMP, BZO, PCP, BAR, MET and OPI, etc. in the fluids.

It is another object of the present invention to provide a "one-device" system to collect, transfer, extract, test and retain a portion of the sample to confirm for various constituents in fluids with constituents in fluids wherein the system further comprising sealing fins to which once fluid enters into the fins, the fins will prevent the fluid from leaking out of the system.

It is another object of the present invention to provide a "one-device" system to collect, transfer, extract, test and retain a portion of the sample to confirm for drugs of abuse in bodily fluids with a sample retention well sealed from the outside allowing samples to be sent later to a laboratory for testing.

Other objectives and advantages of the invention will become apparent from the following detailed disclosure.

BRIEF DESCRIPTION OF THE DRAWINGS

The novel features which are believed to be characteristic of the invention are set forth with particulars in the appended claims. The invention itself, both as to its organization and method of construction and operation, may best be understood by reference to the following description, taking in connection with the accompanying drawings in which:

FIG. 4A is an inner view of the bottom cassette assembly showing micro-sample pores and channels (with absorbent filter material removed) of the present invention;

FIG. 4B is an inner view of the top cassette assembly showing micro-sample pores and channels (with absorbent filter material removed) of the present invention;

DETAILED DESCRIPTION OF THE PREFERRED EMBODIMENTS

Figure 1:
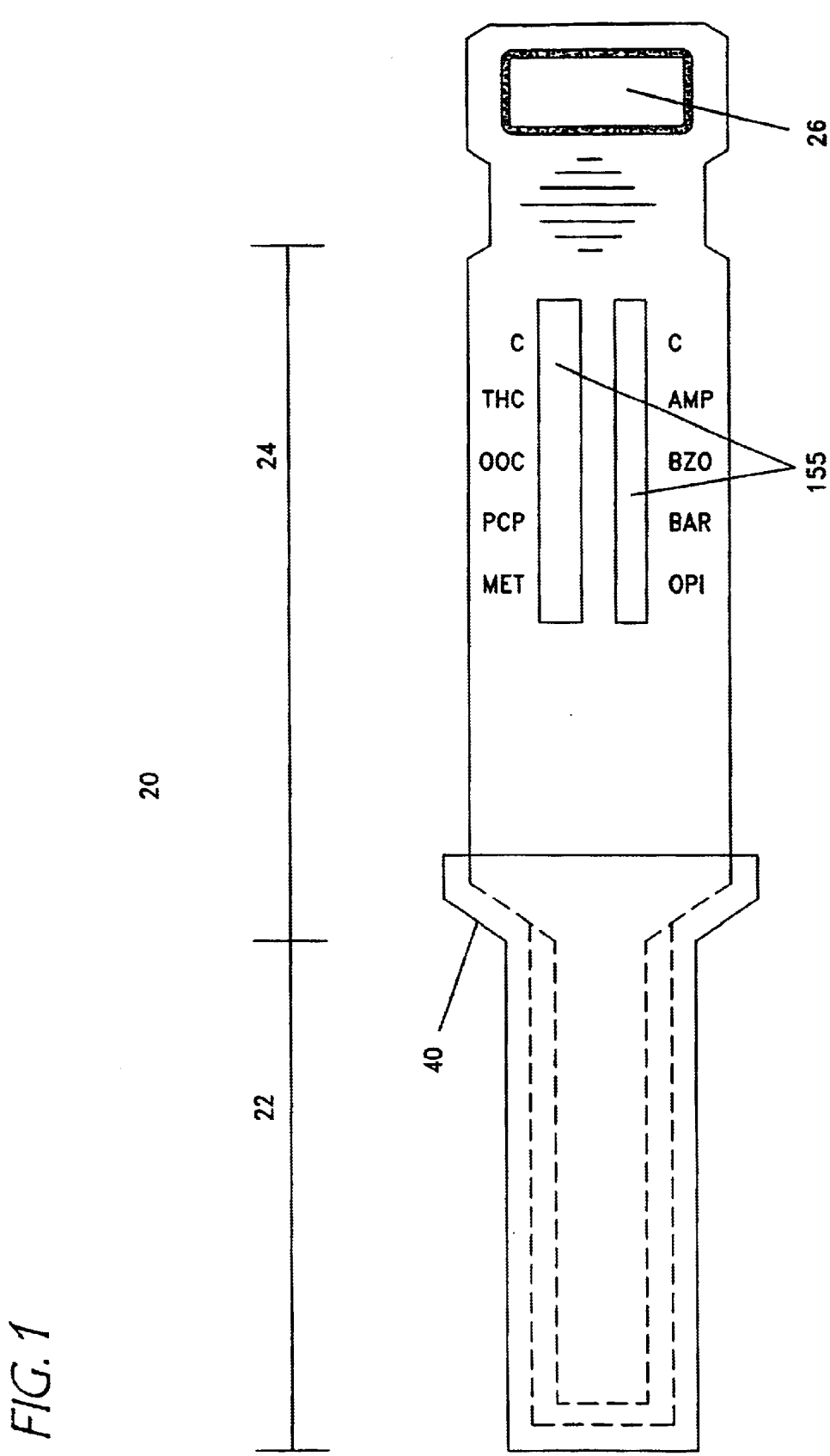
FIG. 1 is an outside view of the entire assembly with cap in place of the present invention.
Figure 2:
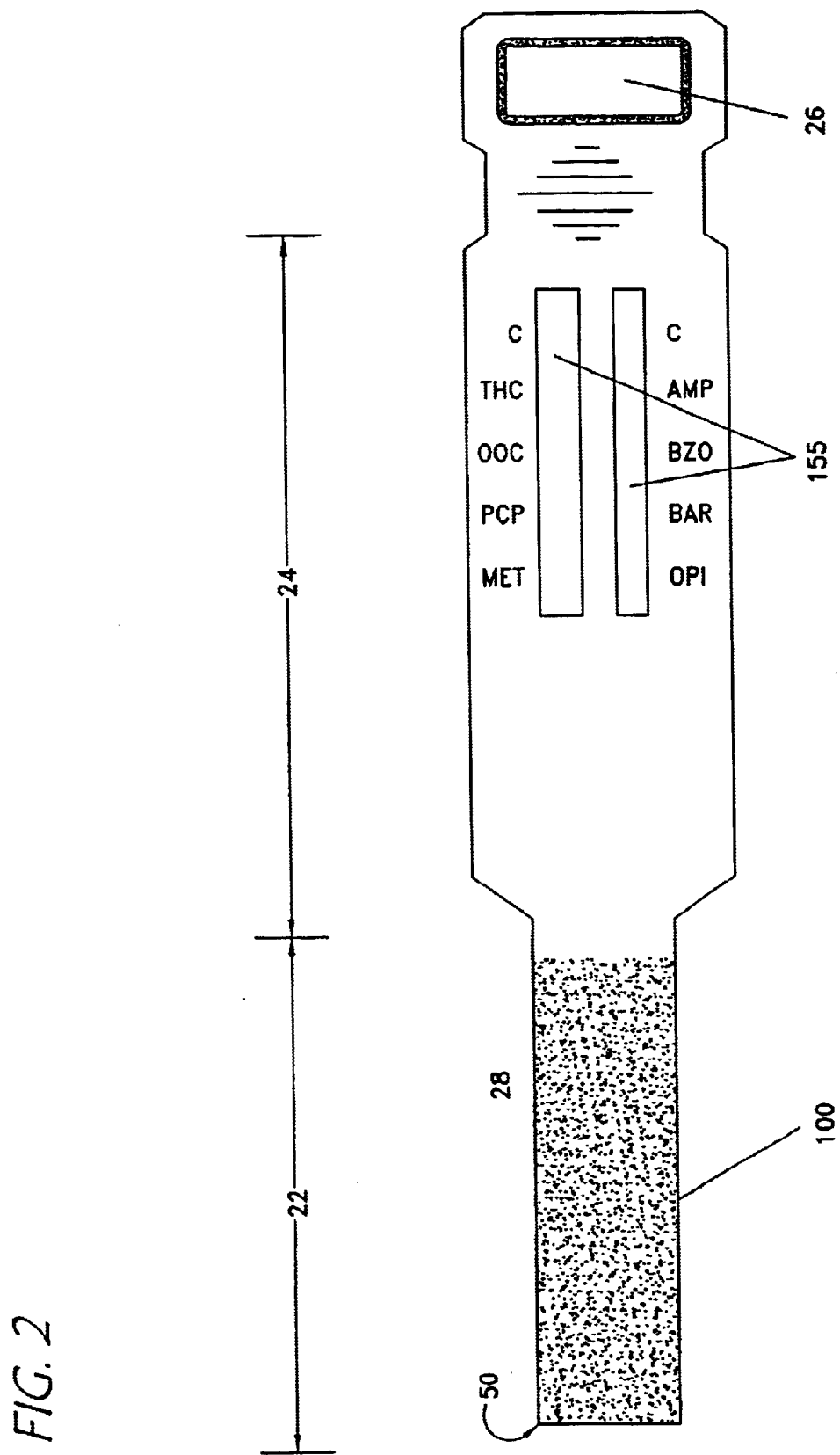
FIG. 2 is an outside view of the entire assembly with cap removed of the present invention.
Figure 3:
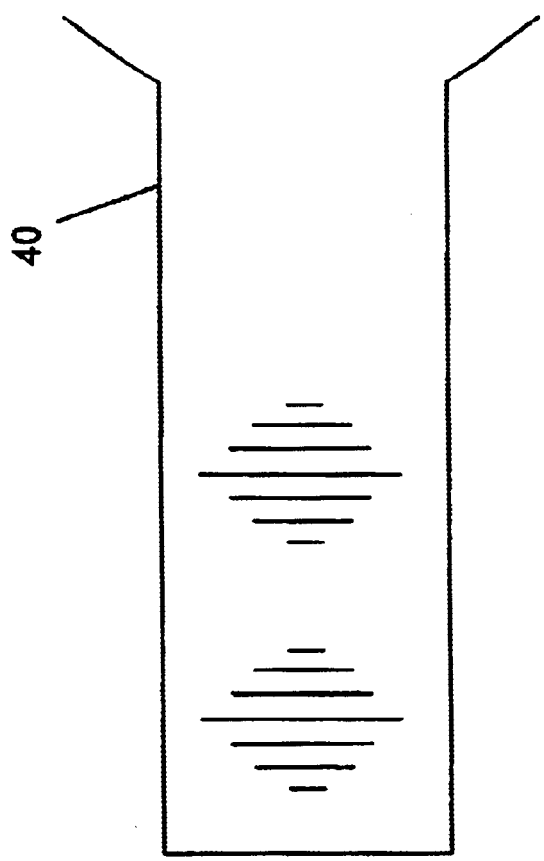
FIG. 3 is an outside view of the cap/extraction device of the present invention.
Figure 6:
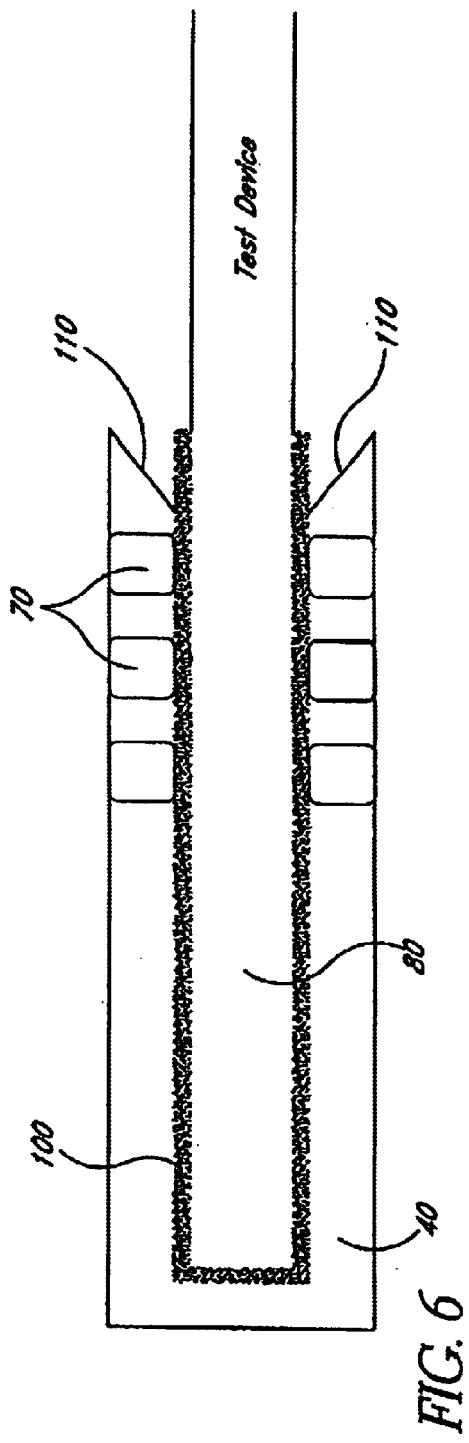
FIG. 6 is a side view of the close up collection/extraction end of device (side-view) showing a set of equal-sized pressure heads of the present invention.
Figure 6A:
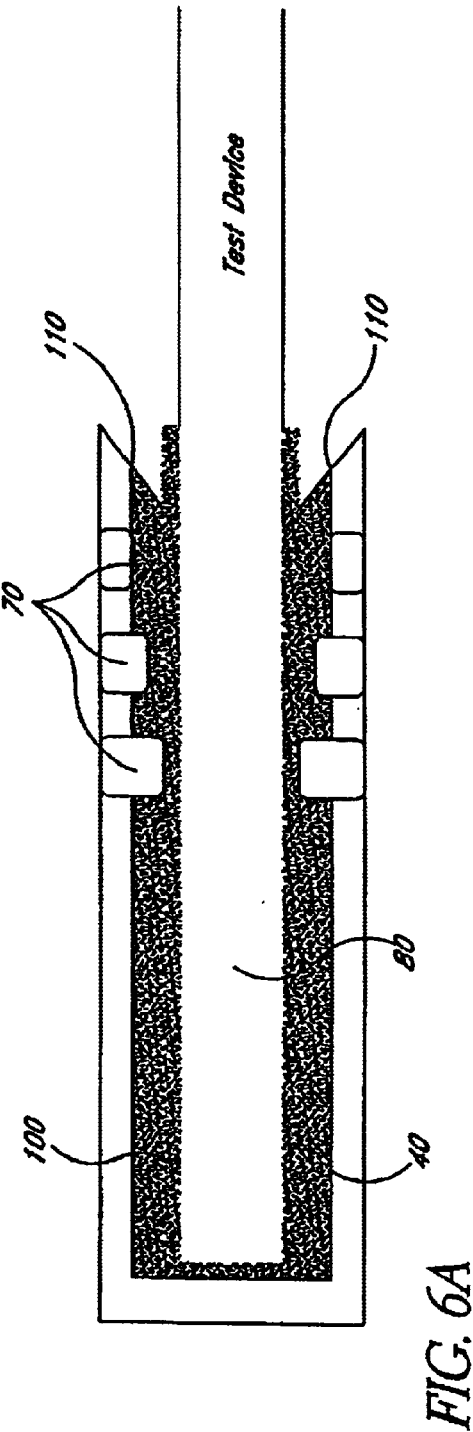
FIG. 6A is a side view of the close up collection/extraction end of device (side-view) showing a set of unequal-sized pressure heads of the present invention.

A collection/test device 20 is normally kept inside a foil container to prevent contamination. During use, it is removed from the foil container. FIG. 1 shows a collection/test device 20 with its cap 40 on. The device 20 normally contains three areas: a collection/extraction area (22), a detection (such as test strips) area (24) and a confirmation sample well cap area (26). The device 20 is generally of a dimension of 100–150 mm long, preferably of 110–130 mm long. The collection area is 40–80 mm long, preferably 50–70 mm long. The confirmation well area and the detection area then make up the rest. The confirmation area is 20–40 mm long, preferably 10–20 mm. FIG. 2 shows the device 20 with its pressure cap 40 removed. Absorbent material 100 (such as gel, foam, fiber glass, cotton, cellulose, rayon or other synthetic materials) in the shape of a pad under the cap 40 is shown. The absorbent pad is used to collect a sample for testing. The pad could be made from any of a number of absorbent materials, such as No. 2 medium cotton roll distributed by Patterson Dental Co. (Minneapolis, Minn.), medical absorbent material by 3M, Saitiou, Sartours and cotton paper manufactured by Schleicher and Schuell in Keene, N.H. To collect a sample, the collection end 50 of the device 20 is placed into a subject's mouth to collect a saliva sample, rub along a subject's arms to collect a sweat sample or put into contact with the material/sample (urine, other bodily fluids, etc.) to be tested. After the sample is collected, the device 20 is then withdrawn from the sample source. The cap 40 is then placed back over the collection end of the device 20. Inside the cap 40 is a series of equal-sized pressure heads such as roller heads 70; or unequal-sized pressure heads such as unequal-sized roller heads 70A (see FIGS. 6 and 6A respectively). For the unequal-sized roller heads 70A, the size of the roller heads are such that more of the sample will be pressed out of the sample's pad as the cap is going over the sampling pad.

Figure 4:
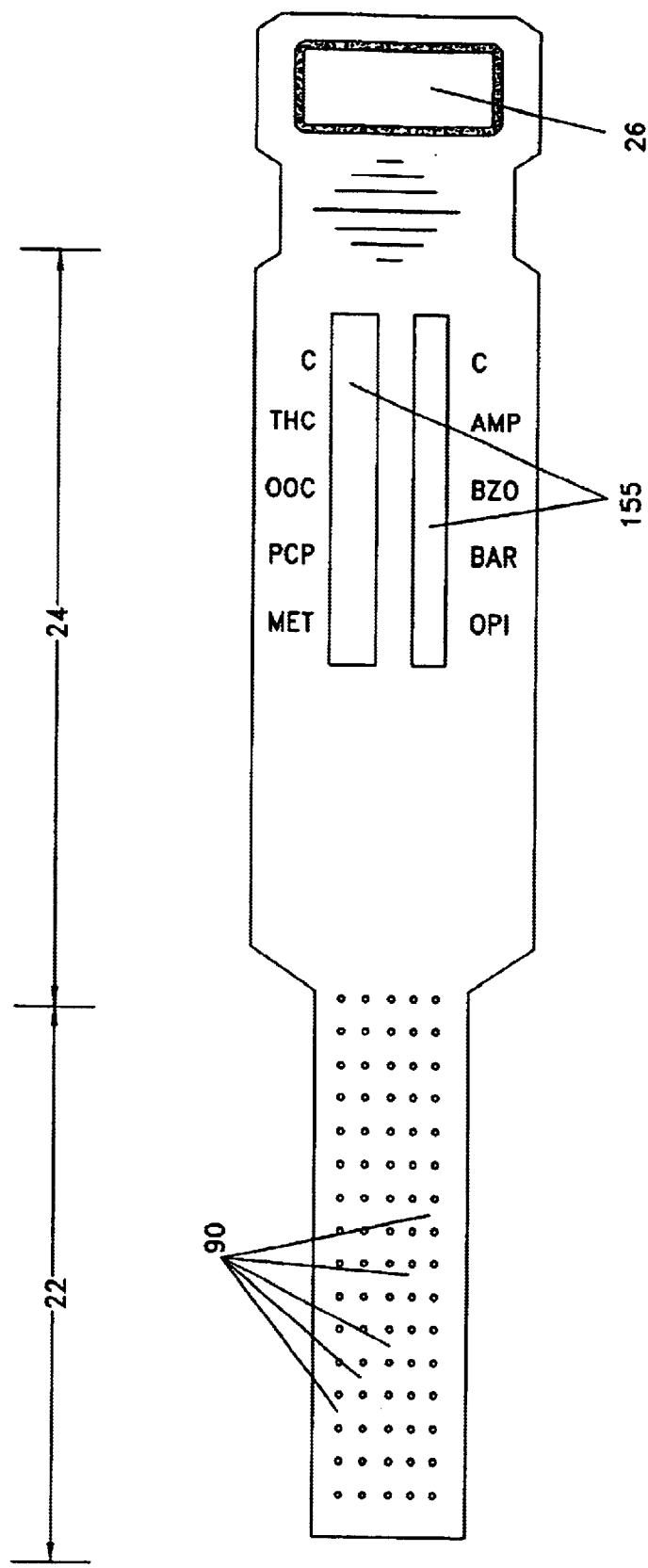
FIG. 4 is an outside view of the entire assembly showing micro-sample pores (with absorbent/filter material removed), of the present invention.
Figure 5:
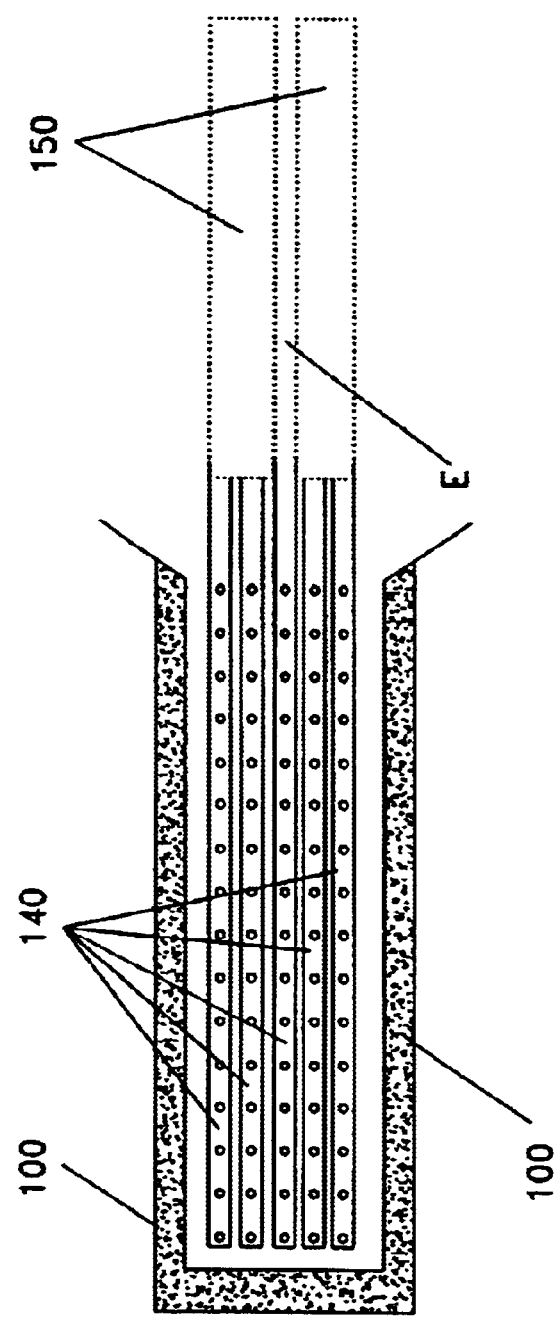
FIG. 5 is a cross-sectional view (lateral cut) of the collection end of the device of the present invention.
Figure 7:
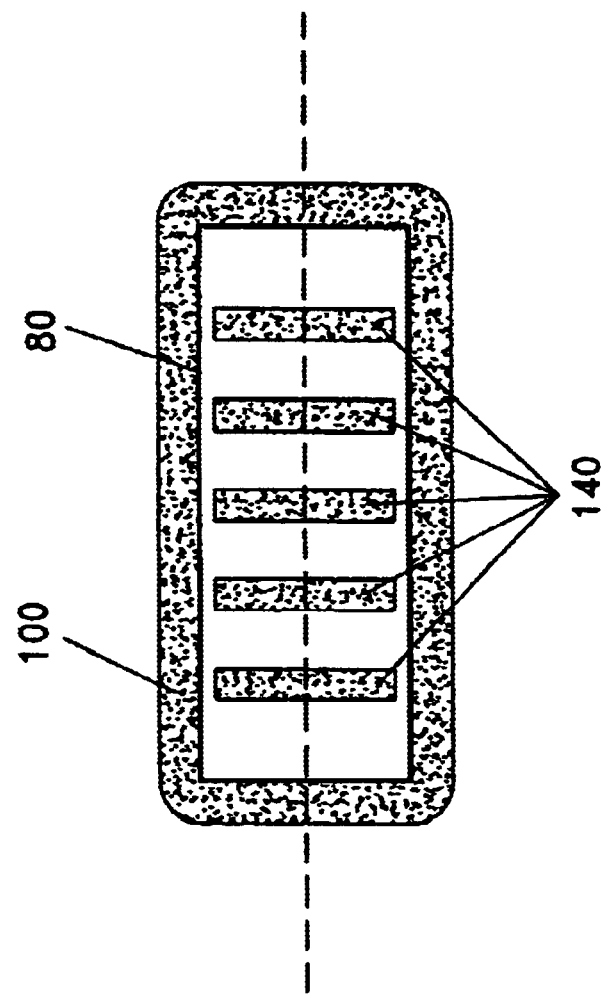
FIG. 7 is a cross-sectional view through collection/extraction end of device of the present invention.

The pressure heads 70 or 70A form a tight column as the collection end of the device 20 passes through the pressure heads 70 or 70A. The sample contained on the absorbent collection material pad 100 is pressed out of the absorbent material pad 100 and into the "core" 80 (see FIG. 7) of the test device through a series of micro-sample pores 90 (see FIG. 4) with diameters ranging from 0.1 to 2 mm, preferably 0.5 to 1.5 mm. Any excess sample that is carried along the top of the absorbent material pad 100 and possibly "leak out" of the extraction cap 40 is directed into the absorbent material by a set of sealing fins 110 (see FIGS. 6 and 6A) at the end of the cap 120. The sealing fins can have smooth (see FIGS. 5, 6 & 6A), concave, convex and undulated edges. The sealing fins 110 are designed to keep all samples inside the cap. The micro-sample pores are connected to a series of micro-channels 140 (see FIGS. 4A and 4B) that carry the extracted sample to the test strip area 24. In the test strip area 24, diagnostic test strips 150 are viewable through test strip windows 155. The test strips 150, include strips such as: for the testing of THC (11-nor-Δ-9-tetra hydrocannabinol-9-carboxylic acid), MOR (Morphine), AMP (amphetamine/methamphetamine), COC (Cocaine), BZO (Benzodiazepines), PCP (1-(1'-phenylcyclohexyl) piperidine), BAR (Barbiturates), MET (Methadone), OPI, etc. (FIG. 4). The sample is "pressed" out onto the test strips 150 by means of an initial capillary action, force and gravity. The sample then makes contact with the diagnostic test strips 150 (such as INSTACHECK test strips cassette produced by Forefront Diagnostics Inc. Laguna Hills, Calif. 92653) and the test is performed. The drug in the sample competes with a drug conjugate immobilized on a membrane support for limited antibody sites on colored microspheres. A colored line on the immunoassay diagnostic test strip indicates the presence or absence of illegal drugs in the sample.

In FIG. 4A, the sample after moving from the collection/extraction area 22, into the test strip area 24, first settle in a sample pad area 25 before moving onto test strip 150. Through micro-flow channels A, B, C, D the sample is being transferred to the bottom cassette assembly containing test strip area 150 for testing. In addition, a portion of the sample can flow through central channel E to the confirmation sample well cap area for storage. Samples stored in confirmation sample well cap area can be sent out such as to a laboratory for confirmation testing later. Similarly, in FIG. 4B, a sample channel F is used to introduce a portion of the sample directly from the collection/extraction area 22 into the confirmation sample well cap area 26. In addition, micro flow channels G, H, I, J is used to transfer the sample from the collection area to the test strip area 150 of the top cassette assembly.

In an alternate embodiment of the device, sealed "vials" 160 of diluents or buffer are placed into the extraction device/test cap 40 or under the absorbent material 100. When the collection end 20 of the device is placed into the cap 40 and forced through the extraction rollers 70, the "vials" 160 are broken and the liquid contained within them is "washed" through the pad and assists in removing the sample from the pad.

What is claimed is:

1. A one-device system for collecting, extracting, and testing a constituents in a fluid specimen therein, said system comprising:
    a testing member having rows of micro-sampling pores leading to a channel containing a detection indicator;
    a super-absorbent material at a collection end of said testing member to collect said fluid specimen;
    a cap containing pressure heads protruding inwardly from an interior sidewall of said cap, the pressure heads defining an opening having a dimension more narrow than that of a corresponding uncompressed width of said absorbent material, and when said collection end is inserted through said pressure heads, said pressure heads being configured to be tightly fitted on said absorbent material to compress said absorbent material and thereby press said fluid specimen from said absorbent material into said rows of micro-sampling pores and then through said channel onto said detection indicator for identification of said constituents in said fluid specimen.

2. A one-device system of claim 1, wherein said fluid is selected from a group comprising saliva, sweat, urine, blood and other bodily fluids.

3. A one-device system of claim 1, wherein said super-absorbent material is selected from a group comprising gel, foam, fiber glass, cotton, cellulose, rayon and other synthetic materials.

4. A one-device system of claim 1, wherein said cap further comprises a row of pressure heads of substantially the same size to press said fluid specimen from said absorbent material onto said detection indicator.

5. A one-device system of claim 1, wherein said cap further comprises a row of pressure heads of different sizes, said pressure heads being configured so that said pressure heads closer to an open of end of said cap protrude less than those pressure heads further from said closed end of said cap in order to fit with varying degrees of tightness against said collection end and thereby to press said fluids from said absorbent material onto said detection indicator.

6. A one-device system of claim 1, wherein said micro-sampling pores are of a diameter with a dimension of 0.1 to 2 mm.

7. A one-device system of claim 1, wherein said micro-sampling pores are of a diameter with a dimension of 0.5 to 1.5 mm.

8. A one-device system of claim 1, wherein said detection indicator is a cassette, containing at least one chemical strip configured to provide an indication of a drug of abuse in said fluid specimen.

9. A one-device system of claim 8, wherein said cassette comprises a plurality of test strips and each test strip in said plurality of test strips is configured to test for a drug selected from a group consisting of THC, COC, MOR, AMP, BZO, PCP, BAR, MET and OPI.

10. A one-device system for collecting, extracting, and testing a constituents in a fluids specimen therein, said system comprising:
    a testing member having rows of micro-sampling pores leading to a cassette comprising a plurality of isolated test channels in said cassette, said plurality of channels being configured to flow said fluid specimen from said micro-sampling pores to a plurality of test strips, each of said plurality of channels housing one of said plurality of test strips for testing drugs of abuse;
    a super-absorbent material at a collection end of said testing member to collect said fluid specimen;
    a cap containing pressure heads protruding inwardly from an interior sidewall of said cap, the pressure heads defining an opening having a dimension more narrow than that of a corresponding uncompressed width of said absorbent material, and, when said collection end is inserted through said pressure heads, said pressure heads being configured to be tightly fitted on said absorbent material to compress said absorbent material and thereby press said fluid specimen from said absorbent material into said rows of micro-sampling pores and then through said plurality of channels to said plurality of test strips, the test strips being configured to provide an indication of a drug of abuse in said fluid specimen, at least two of said plurality of test strips being configured to test for differing drugs of abuse.

11. A one-device system of claim 1, wherein said system further comprises sealing fins located between said cap and said testing member at a position proximate to an open end of said cap, said sealing fins forming a seal between said testing member and said cap, said sealing fins being configured to, when said fluid specimen is entered into said system, substantially prevent said fluid specimen from leaking out of said system.

12. A one-device system of claim 1, wherein said system further comprises a separate confirmation sample well, sealed from the outside and allowing a portion of said fluid specimen to be retained for further testing later.

13. A one-device system of claim 1, further comprising vials of liquid located in said cap, the vials being located and configured to be crushed by said pressure heads and release said liquid into said super-absorbent pad.

14. A one-device system of claim 1, further comprising vials of liquid located on said testing member, the vials being located and configured to be crushed by said pressure heads and release said liquid into said super-absorbent pad.

* * * * *